(12) United States Patent
Wearne (10) Patent No.: US 11,456,067 B2
(45) Date of Patent: Sep. 27, 2022

(54) PLATFORM AND SYSTEM FOR USE IN THERAPEUTIC PROCEDURES

(71) Applicant: CARETECH SERVICES PTY LTD, Perth (AU)

(72) Inventor: David Wearne, Booragoon (AU)

(73) Assignee: CARETECH SERVICES PTY LTD, Perth (AU)

(*) Notice: Subject to any disclaimer, the term of this patent is extended or adjusted under 35 U.S.C. 154(b) by 0 days.

(21) Appl. No.: 17/198,524

(22) Filed: Mar. 11, 2021

(65) Prior Publication Data

US 2021/0217507 A1 Jul. 15, 2021

Related U.S. Application Data

(63) Continuation of application No. 16/969,323, filed as application No. PCT/AU2019/050067 on Jan. 30, 2019.

(30) Foreign Application Priority Data

Feb. 15, 2018 (AU) .................................. 2018900475

(51) Int. Cl.
*G16H 20/17* (2018.01)
*G16H 40/67* (2018.01)
(Continued)

(52) U.S. Cl.
CPC ............. *G16H 20/17* (2018.01); *A61J 1/06* (2013.01); *G06N 20/00* (2019.01); *G16H 40/67* (2018.01); *A61J 2205/60* (2013.01)

(58) Field of Classification Search
CPC .... A61M 5/5086; A61M 15/00; G06Q 50/00; G06Q 10/08; G16H 10/65; G16H 20/13; G08B 7/066
(Continued)

(56) References Cited

U.S. PATENT DOCUMENTS 8,044,778 B2 * 10/2011 Monroe ................. A61B 90/98
340/426.19
8,234,129 B2 * 7/2012 Michon ................. G06Q 40/08
705/3
(Continued)

FOREIGN PATENT DOCUMENTS

WO 2014028936 2/2014
WO 2017106247 6/2017

OTHER PUBLICATIONS

Google patents search, Feb. 23, 2022 (Year: 2022).*
ip.com search, Feb. 22, 2022 (Year: 2022).*
ip.com search, May 28, 2022 (Year: 2022).*

*Primary Examiner* — Dilek B Cobanoglu
(74) *Attorney, Agent, or Firm* — Ballard Spahr LLP (57) ABSTRACT

A portable therapeutic platform for use in a therapeutic procedure including: (a) at least one compartment for holding at least one therapeutically effective item required to conduct the therapeutic procedure; and (b) at least one electronic communications device for receiving and transmitting information about an environment surrounding and including the platform. The use of the platform is conveniently managed by a system which transfers information about the environment surrounding and including the platform between the electronic communications device and a computer system including a processor which processes the information; and initiates a control response to the processed information. The platform and system are suitable for use to address a range of public health issues and as a countermeasure to biosecurity threats.

11 Claims, 6 Drawing Sheets

(51) Int. Cl.
*G06N 20/00* (2019.01)
*A61J 1/06* (2006.01)

(58) Field of Classification Search
USPC .............. 705/3, 2; 340/426.19; 235/383, 385
See application file for complete search history.

(56) References Cited

U.S. PATENT DOCUMENTS

| | | | | |
|---|---|---|---|---|
| 8,332,240 | B1* | 12/2012 | Garver | G16H 70/40 |
| | | | | 705/3 |
| 8,376,228 | B2* | 2/2013 | DeVet | G06Q 10/08 |
| | | | | 235/383 |
| 9,171,280 | B2* | 10/2015 | Gitchell | A61J 1/00 |
| 9,326,742 | B2* | 5/2016 | Hirschman | A61B 6/032 |
| 9,550,031 | B2* | 1/2017 | Van Sickle | A61M 15/00 |
| 9,566,395 | B2* | 2/2017 | Denny | G08B 1/08 |
| 9,672,328 | B2* | 6/2017 | Saint | G16H 20/13 |
| 9,973,611 | B2* | 5/2018 | Pether | A61J 7/0481 |
| 10,102,923 | B1* | 10/2018 | LaBorde | G06K 7/10366 |
| 2003/0038047 | A1 | 2/2003 | Sleva et al. | |
| 2003/0086338 | A1* | 5/2003 | Sastry | G16H 20/13 |
| | | | | 368/10 |
| 2006/0138221 | A1* | 6/2006 | Swan | G06Q 10/08 |
| | | | | 235/383 |
| 2006/0154642 | A1* | 7/2006 | Scannell, Jr. | G08B 7/066 |
| | | | | 455/404.1 |
| 2007/0131573 | A1 | 6/2007 | Boyles | |
| 2009/0128330 | A1 | 5/2009 | Monroe | |
| 2010/0066509 | A1* | 3/2010 | Okuizumi | A61J 1/035 |
| | | | | 340/10.5 |
| 2012/0203573 | A1* | 8/2012 | Mayer | G16H 20/13 |
| | | | | 705/3 |
| 2013/0137607 | A1 | 5/2013 | Ghatak | |
| 2014/0278468 | A1* | 9/2014 | Mayer | G16H 40/67 |
| | | | | 705/2 |
| 2016/0022361 | A1 | 1/2016 | Khajavi | |
| 2017/0076068 | A1 | 3/2017 | Dobbles et al. | |

* cited by examiner

PLATFORM AND SYSTEM FOR USE IN THERAPEUTIC PROCEDURES

CROSS REFERENCE TO RELATED APPLICATIONS

This application is a continuation of U.S. application Ser. No. 16/969,323, filed Aug. 12, 2020, which is a U.S. National Phase Application of International Application No. PCT/AU2019/050067, filed Jan. 30, 2019, which claims benefit of priority to Australian Patent Application No. 2018900475, filed Feb. 15, 2018, entitled "A Platform and System for Use in Therapeutic Procedures," all of which are incorporated herein in their entireties.

FIELD OF THE INVENTION

This invention relates to a platform and system for use in a therapeutic procedure, for example, for the administration of at least one injectable by injection. Such a platform and system is, amongst other applications, suitable for use by 1) patients requiring intravenous, intramuscular or other forms of drug or vaccine administration including by injection by bifurcated needle, for example for treatment of chronic disease such as insulin dependent diabetes or vaccination such as cholera or smallpox vaccination in single or multiple episodes; and/or 2) patients requiring vaccination against disease, particularly in an outpatient setting; and/or 3) entities controlling treatment of patients, typically in an outpatient setting, and which can collect and process data collected from the platform and system to optimise patient health, including in the context of a public health crisis or emergency where urgent management action, for example of vaccine and/or reagent delivery to patients, is required. In this regard, the therapeutic platform and system may also be used in a biosecurity countermeasure setting with application to the protection of populations from harmful biological or biochemical threats involving viruses or other modes of biological attack.

BACKGROUND ART

It is well recognised that certain communicable and chronic diseases require pre-emptive, timely, targeted and/or regular administration of vaccines and medications. Examples of therapeutic procedures range from the treatment of insulin dependent diabetes to communicable disease inoculation often by vaccination to procedures targeted at addressing a public health crisis or emergency. Practically, such medicament or vaccine procedural administration, though effectively a therapeutic procedure, oftentimes does not always occur in a therapeutic environment though, given this limitation, should nevertheless desirably occur in a manner providing maximum therapeutic benefit and safety to the patient, health care worker and the community. Particular issues of concern here are dispensing errors generally (which become more problematic in the case of a biosecurity threat or public health emergency where control over the accuracy of identification of the correct medicament or vaccine and its dosage in an environment where involvement of non-medically trained staff is likely to be essential) and, more specifically including authenticity of a medicament or vaccine, dosage of the medicament or vaccine; quantum and nature of any required reagent and/or diluent for a medicament as well as appropriate delivery components; and handling of needles and sharps.

A first key class of problem arises from the lack of control over such therapeutic procedures performed in a non-therapeutic environment. Multiple inherent risks arise from the provision of incorrect and/or incomplete delivery of the prescribed items for performing the therapeutic procedure and the associated costs to both the patient and community. This is especially so in the case of any procedure involving intravenous injection. In such cases, apparatus for conveying injectables/diluents and needles and syringes and/or cannulas has typically been compartmentalised from delivery, often as separate and loose items, for conducting the multiple facets of the intended procedure, as well as the disposal management container for the sharps. So, injectables, needles, syringes and cannulas may be available to an individual, in a form of pack, but there is a lack of control over, and information on, variables such as the nature of the injectable, administered dosage of injectable, the amount of diluent used and the use of other items required for the procedure.

Another class of problem can arise from the way in which items are packaged for a therapeutic procedure. Safety and efficacy depend on a pack containing the correct items for a procedure. However, errors can occur and the wrong items, whether physical or pharmaceutical items, can be packaged together. While this is more likely to be an issue where packaging occurs in an informal setting without adequate quality assurance, such errors can also occur in more sophisticated therapeutic packaging settings and presents a problem for secondary packaging in particular.

Both classes of problem raise safety issues but the lack of information about what actually happens when such procedures are performed also means that, though well intended, the procedure is not actually tailored to the needs of patients. Alternatively, the lack of information leads to an inability to compensate for poor patient performance of the procedure or the opportunity to make the procedure safer and more efficient.

Such problems become more acute in the context of biosecurity where such packs may require to be produced on an urgent basis to protect a population from a biochemical or biological threat, particularly an unidentified threat which may include a viral threat or another mode of biological attack. In such cases, therapeutic packs may carry antidotes, possibly in the form of vaccines, to immunise the population. Medicaments to counter the biosecurity threat may also be provided, typically under the supervision of an entity such as a government agency. Such packs should be used in a coordinated fashion with the antidote being customised to a threat that may be changing in real time, for example in the form of a mutating virus. In such cases, there is a need for the pack manufacturing centre to modify the antidote, or more typically receive a modified antidote from another source, for delivery to the threatened population creating a significant logistics challenge. However, to the knowledge of the Applicant, a fast response to this problem is not possible with current technology.

It is an object of the present invention to provide a platform and system for use in a therapeutic procedure that flexibly addresses, at least to some extent, the informational deficit, control, logistical and packaging issues which can hinder safe and efficacious performance of a range of therapeutic procedures including in the context of an urgent response to a biosecurity threat or other public health crisis or emergency.

SUMMARY OF THE INVENTION

With this object in view, one embodiment of the present invention provides a portable therapeutic platform for use in a therapeutic procedure and comprising:

(a) at least one compartment for holding at least one therapeutically effective item required to conduct the therapeutic procedure; and (b) an electronic communications device for receiving and transmitting information about an environment surrounding and including the platform. One form of platform is a pack as described below; however though the terms may be used interchangeably herein, this is not intended to be limiting.

Another embodiment of the present invention provides a system for managing the use of a portable therapeutic platform for a therapeutic procedure comprising the steps of:

(a) providing at least one platform comprising at least one compartment for holding at least one therapeutically effective item required to conduct the therapeutic procedure and an electronic communications device for receiving and transmitting information about an environment surrounding and including the platform;

(b) transferring information about the environment surrounding and including at least one platform between the electronic communications device and a computer system including a processor which processes said information; and (c) initiating a control response to said processed information.

By "therapeutically effective" is intended that the item, for example a pharmaceutical substance, a diluent or physical item such as a syringe or cannula, has an effect on the patient. Desirably, the effect improves or protects patient health but is not limited to these situations. The effect, in this context, may also be detrimental though the collection of information about usage of the procedural pack may assist in improvement of the health of the patient or future patients.

The electronic communications device desirably communicates with the computer system through a wireless communications network, desirably a secure wireless communications network, so that information and/or instructions (one form of control response to information received from therapeutic packs) can be communicated between the portable platform or pack and the computer system. The computer system would typically form part of a control centre for the therapeutic procedure and would, in the case of a public health crisis or emergency including a biosecurity threat, also typically be managed by a government agency. Information may include, without limitation, information about the use of the pack which may include sensors detecting when, how and/or where the items contained within the pack are used or sensors indicating that the pack should be used. Instructions could include, without limitation, opening the pack or indicating when use is required. For example, the therapeutic packs could be issued to protect a population against a possible biosecurity threat. However, the relevant authority may not yet have evidence that the population must use the therapeutic pack for protection. When such evidence is received, instructions may be issued for the population or segment(s) of that population, segments being determined by geographical location or processing of usage data as described below. Such instructions, preferably sent through a wireless communications network from the computer system to individual platforms or packs, could include activation of the therapeutic pack, for example by providing access to the pack. This allows greater precision over the therapeutic response to the threat. The packs may include a messaging system or may be used in co-operation with a messaging system, for example as provided by a mobile phone or smart device with an identifier correlated with the pack and unique identification code(s) provided for electronic communication device(s) included within a pack.

Where many such therapeutic packs are deployed, perhaps in response to an epidemic or public health crisis, including response to a biosecurity threat, the computer system may receive multiple informational inputs from multiple therapeutic packs showing how, when and where they are used, i.e. tracking information. Such information may be processed by the processor to determine strategies for use of the pack both in real time and in future scenarios and which require initiation of a control response. Such information would desirably enable statistical process control and greater precision over the response to the biosecurity threat or other public health crisis through deployment of therapeutic packs as described herein. Statistical process control may be supplemented by use of machine learning techniques by processing of information by the processor to improve the efficacy of deployment of therapeutic packs as described herein while minimising costs, however measured, of such deployment or, indeed, non-deployment. The computer system may also control the logistical mode of deployment of packs to a target population, for example by autonomous vehicle, robot, drone or like computer controllable transport means which is particularly advantageous where the threat is highly contagious, for example a viral infection.

Various communication methodologies are suitable with communication through a wireless network being preferred if not essential. However, provision for downloading usage information from the therapeutic procedural pack could be made. An electronic communications device included within the pack may form part of a passive or active RFID system in which case at least one RFID chip and antenna may be included within a pack. RTLS or other electronic tracking and positioning systems may be used as an alternative to RFID systems. Information may be communicated between the therapeutic pack and the database and processed by the processor in real time which may enable assistance to be provided to the patient during the procedure, conveniently through a smartphone or similar device, noting that—in some instances—such devices forming part of a wireless communications network (such as Wifi or the internet) that can also usefully be used to convey information and instructions to and from a pack could be configured to form the platform.

The platform, conveniently in the form of packs as alluded to above, may also include one, or a plurality of, analytic devices—such as microfluidic devices and associated integrated circuits—which allow analysis of items included within the pack or analysis of the environment surrounding and including the pack. Such an analytic device may test diluents, injectables or pharmaceutical compositions generally to check that such are safe for administration in terms of chemical composition and dosage. When coupled with the electronics communication device(s), this may allow remote sensing and hazard warnings to be issued to the patient potentially in real time. Such analysis may also provide information on stability of pharmaceutical compositions which may be matched with pack usage information to enable improvement of stability or matching stability profiles to usage patterns for the pack which may reduce costs in producing therapeutic packs. In a biosecurity threat context, the analytic device may determine whether that threat exists and whether the therapeutic pack may be appropriately deployed to counter the threat. This feature addresses a scenario in which authorities may have sufficient knowledge to determine that therapeutic packs should be provided to a population but insufficient information about the scale and spread of the threat to advise which members of the population need to use the pack (noting that the medicaments or other items therein have a cost and wastage of packs and costs is desirably prevented).

The computer system may also initiate a control response in terms of modifying a step in a pack manufacturing process, as described below, so that packs include the necessary therapeutically effective item(s) to counter the threat. In one embodiment, the computer system could control a machine or manufacturing plant to produce packs customized to the identified threat. For example, the computer system could control a 3D printing facility or injection moulding plant to produce packs with compartments and provided with items including an antidote corresponding to a therapeutic procedure to be conducted. In the case of a threat in the form of a mutating virus, the computer system may receive informational updates from a computer system storing data about research and development into the antidote, likely to be occurring in real time in the case of a biosecurity threat or other public health crisis. This allows a real time response to manufacturing capability and reduction in the lag to an efficacious response identified in the background discussion. Such could include a vaccine, for example developed using accelerated techniques as described for example in WO 2018176103, the contents of which are hereby incorporated herein by reference One preferred portable therapeutic pack of the form above described is suitable for use in a therapeutic procedure including administration of a medicament or vaccine, optionally by injection in single or multiple episodes, and comprises a container for holding a plurality of items required to conduct the therapeutic procedure; and a plurality of compartments located within the container, each compartment corresponding, desirably strictly corresponding, with an individual item required for the therapeutic procedure and including a compartment for accommodating the at least one medicament or vaccine. The size of the container and number of the compartments located within the container in this embodiment is dependent on the therapeutic procedure with a determined dosage of the medicament or vaccine. Such configuration of the container is aimed at ensuring safe dosages during the therapeutic procedure.

The plurality of items, each item highly desirably being accommodated within a dedicated compartment within the container, may be selected from a combination of any of the following: one or more ampoules containing diluents and/or injectable medicament, one or more vials containing vaccines including lyophilised or 'freeze dried' drugs and/or vaccines and/or reagents and/or diluents as known in the art; one or more needles or other appropriate sharps, cannulas and syringes which should be aseptically packaged, and swabs, and specific sharps disposal devices to enable safe disposal of syringes and needles after use with the therapeutic procedure pack conveniently being for single use but configurable for multi-dose use as well.

Conveniently, therapeutic packs may include one or more vials, ampoules and cartridges for holding injectables and/or diluents. In such case, one or more of the container, vials, ampoules and cartridges for holding advantageously include a sensor and/or electronic communications device, as above described, to also provide an "electronic safety net" for tracking of the vessel containing the injectable/diluent, and the procedural pack. To that end, the therapeutic procedural pack and, more particularly the container thereof, may include the at least one electronic communications device with an associated power source whether battery (single use or rechargeable) or renewable, for example a photovoltaic cell. An RFID chip and antenna may also be located within each vial, ampoule or cartridge for holding an ampoule, conveniently being accommodated within the compartment provided with an RFID chip with a unique identification code for each which may be used for tracking and, at an earlier stage, for authentication of the item and/or ensuring that the correct item is placed within a compartment during the manufacturing process. The number and nature of communications devices will depend on factors such as: the informational requirements of the computer system, the necessary level of precision required by the therapeutic procedure, for example as measured by the SIL system and/or the desired degree of control over conducting the therapeutic procedure. Tracking data, as classified above, may be correlated with patient and dosage information, use and compliance, within the scope of the prescribed therapy or program and for injectable life cycle management, security, supply and inventory management purposes. Such data may advantageously be used in controlling and/or improving efficacy of the therapeutic packs and may be used as a basis for statistical process control over the manufacture, deployment and use of the therapeutic packs. Where RFID tracking is used, for example, there is likely—in the case of a public health emergency—to be a need to process data from multiple RFID chips or tags, potentially presenting an identification problem. An anti-collision algorithm, such as binary encoding, or other algorithm, for example as described in Liu and Su, "An Anti-Collision Algorithm for RFID based on An Array and Encoding Scheme", (2018) the contents of which are hereby incorporated herein by reference may be required.

The platform and system as described above offers enhanced security in a number of ways. With linkage of communications devices to critical items included or to be included within a procedural pack, e.g. RFID chips or tags, the risk of counterfeiting of critical items and especially medicament or vaccine components, can be minimised and greater assurance on authenticity of vaccines, medicaments and/or reagents for use in the therapeutic procedure can be obtained. The capacity for increased control over the use of packs also simplifies some logistical challenges and enhances security. In this regard, various code including Blockchain code can also be used to process the data and enhance the security of such information as well as the item authentication process, for example the production and supply history of the item may be checked through a Blockchain ledger methodology. In addition, greater verification and authentication of the items to be contained within packs should also be increased. Electronic tracking and data stored within the computer system as described above has a value and may be used as a form of currency.

The container desirably includes features to prevent improper use, packaging errors, and dispensing errors, particularly to avoid and prevent the procedural pack containing the incorrect set of items for a prescribed therapeutic procedure. To this end, the plurality of compartments of the container may be configured to accommodate only the prescribed set of items. For example, for a given container and therapeutic procedure, each compartment may be configured with a unique form matching the required items for the therapeutic procedure. For example, a compartment may be configured only to accommodate and/or engage a particular size, colour, form or otherwise of ampoule, vial; or cartridge for holding an ampoule or vial. Where an item is attached, at the time of distribution, to its compartment, the attachment requires matching the shape, size, colour or otherwise with the corresponding pack compartment. For example, if threadable attachment is used, a complementarily threaded compartment would match the thread and size of the required item.

The container and disposal component of the therapeutic procedural pack can be made of a suitable polymer or combination of polymers or other materials, conveniently manufactured in a cost effective process such as injection moulding. The therapeutic procedural pack may include a wrapper for maintaining aseptic conditions of the contents until required for administration to a patient. The therapeutic procedural pack is also intended to be supplied with instructions, written and/or otherwise, as to its correct use and as a method of dispensing other information and messaging if required. This may also include any other material/s that might be required or desirable to be provided with the packs and medicaments in accordance with government, program and compliance regulations.

A method of manufacturing such portable therapeutic platforms or packs, as above described, forms another aspect of the invention. For example, the present invention provides a method of manufacturing a portable therapeutic procedural pack for use in a therapeutic procedure including administration of at least medicament and comprising:

(a) a container for holding a plurality of items required to conduct the therapeutic procedure; and (b) a plurality of compartments located within the container, each compartment corresponding with an individual item required for the therapeutic procedure wherein container and compartments are manufactured from plastics by injection moulding and tooling for manufacturing the procedural pack is configured and operated dependent on the therapeutic procedure and determined dosage of the at least one medicament. Where the pack includes at least one electronic communication device, a computer system advantageously controls the manufacturing process to efficaciously respond to a biosecurity threat or other public health crisis based on informational inputs received in real time from a plurality of platforms or packs for example as described above.

The therapeutic procedural platform and system as described above addresses a range of health, packaging and logistical issues confronted during administration of medicaments or vaccines in a non-therapeutic environment, potentially in the context of a biosecurity threat or other urgent public health crisis, and does so in a safe and cost effective manner.

SHORT DESCRIPTION OF THE DRAWINGS

The platform and system of the invention may will be more completely understood from the following description of a preferred and non-limiting embodiment thereof made with reference to the accompanying drawings in which.

DETAILED DESCRIPTION OF PREFERRED EMBODIMENTS

Figure 9:
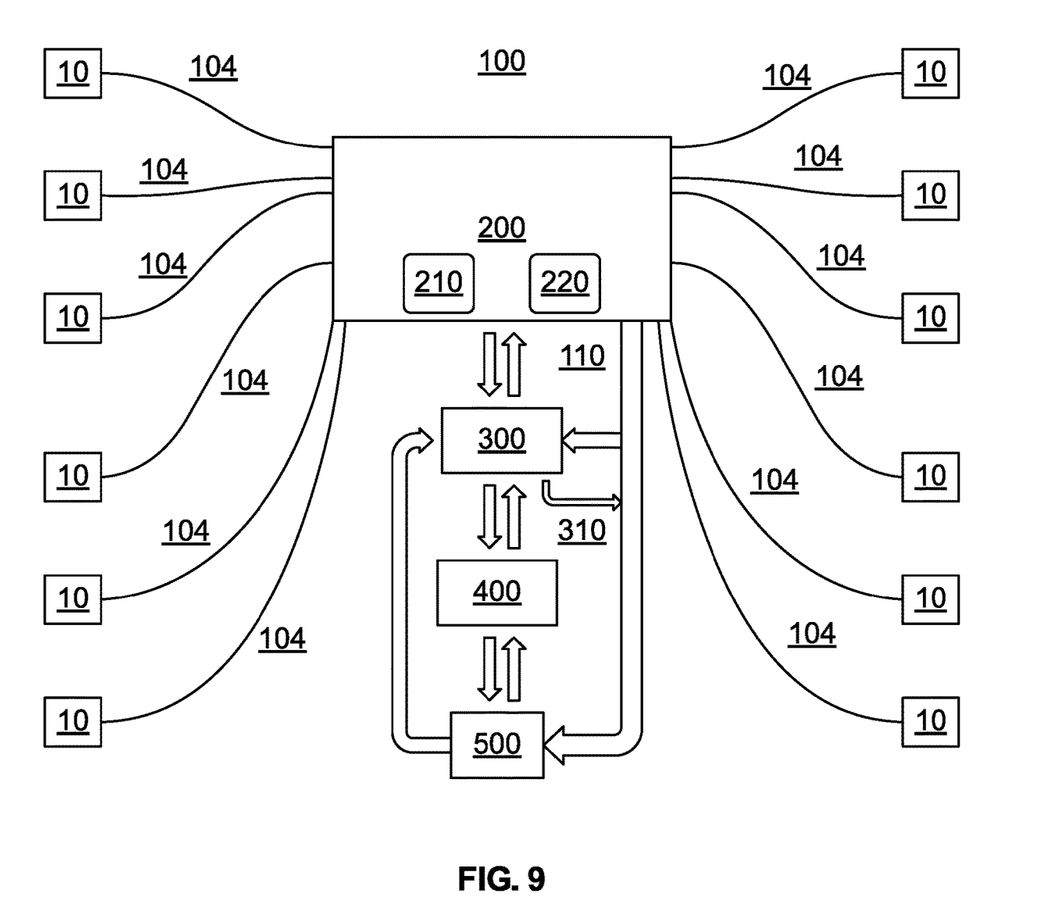
FIG. 9 is a block diagram schematically showing the system of an embodiment of the present invention and involving one or more of the therapeutic procedural packs illustrated with reference to FIGS. 1 to 8.

Referring now to FIGS. 1 to 3 and 5 to 8, there is shown a therapeutic procedural pack 10 for use in a therapeutic procedure suitable for administration of an injectable medicament or vaccine. The medicament could, for example, be insulin, for administration to insulin dependent diabetics. Procedural pack 10 includes the medical items necessary to conduct this therapeutic procedure. The skilled person will understand that procedural pack 10 is not limited in application to treatment of diabetes and procedural packs 10 may be used to counter a number of public health issues and as a countermeasure to threats such as biosecurity threats as described further below. The therapeutic procedural pack 10 is supplied with instructions, written or otherwise, as to its use. The instructions also include any other material that is required to be provided with medical devices and medicaments under government regulations. The procedural pack 10 could be provided with a messaging system, for example a wireless text messaging system, to allow it to receive communications from a control centre managing the therapeutic procedure through communication channels 104 (which may be secure) as shown in FIG. 9 and described further below.

Procedural pack 10 includes a generally rectangular container 12 with a plurality of upward facing compartments 13, 14, 15 and 16 for holding items required to conduct the therapeutic procedure and including syringe 20, disposal device 30; stopper 35; and ampoules 140A and 142A secured within cartridges 40, 42. The number, spacing and sizing of compartments are strictly dictated by the items, medicaments and dosages required in the therapeutic procedure. Each compartment is separated from its neighbouring compartment by a wall or partition, i.e. walls or partitions 13A, 15A and 16A.

The container 12 has two compartments 13 and 14 taking up a substantial portion of the container 12. Compartments 13 and 14 are separated by a partition 13A. Compartments 13 and 14 accommodate a disposal device 30 for disposal of the syringe 20 and associated needle after use, for example the disposal device as described in Australian Patent No. 2001250170, the contents of which are hereby incorporated herein by reference. Disposal device 30 has a syringe retention portion 32 as well as a syringe barrel encapsulating portion 30A and a needle encapsulating portion 30B. The base of compartment 14 includes an RFID chip/transmitter 17 assigned with a unique identification code, the purpose of which is described below. RFID chip/transmitter 17 can be included during moulding of container 12.

For convenience, syringe 20 can be loosely packed within device 30, which thus functions as a transport device, on fabrication of therapeutic procedure pack 10 and prior to use. The design of syringe 20 is not important and the therapeutic procedural pack 10 is intended to accommodate various syringe designs. Syringe cap 20A is removed to allow access to the needle (not shown) for injection. Syringe 20 is here intended to draw on medicament or vaccine and diluent (such as sterile water) contained within respective ampoules 140A and 142A. However, the syringe could also be pre-filled with the necessary liquid for the therapeutic procedure. Syringe barrel encapsulating portion 30A is cylindrical and may be neatly fitted through the partition 13A to prevent movement during transport. The position of syringe encapsulating portion 30A is offset from a centre longitudinal axis of container 12.

Figure 4:
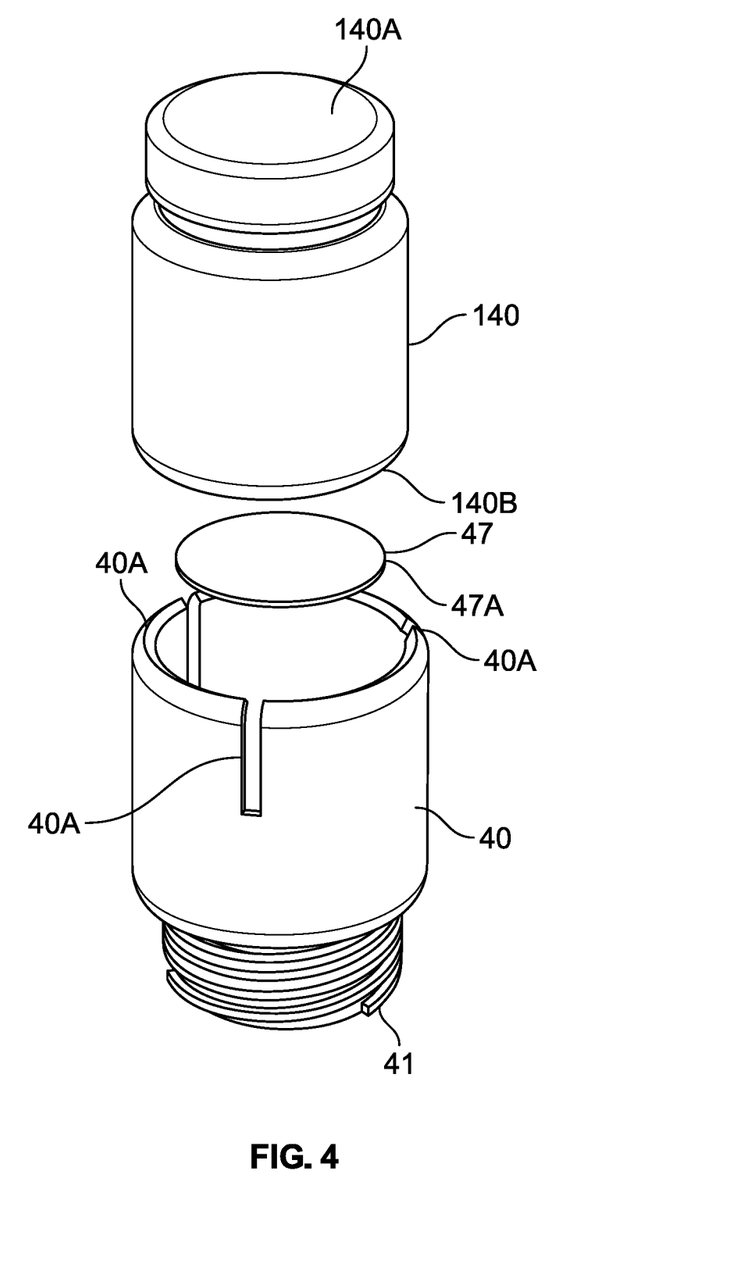
FIG. 4 shows a side orthogonal view of an ampoule and cartridge as shown in FIGS. 2 and 3.
Figure 5:
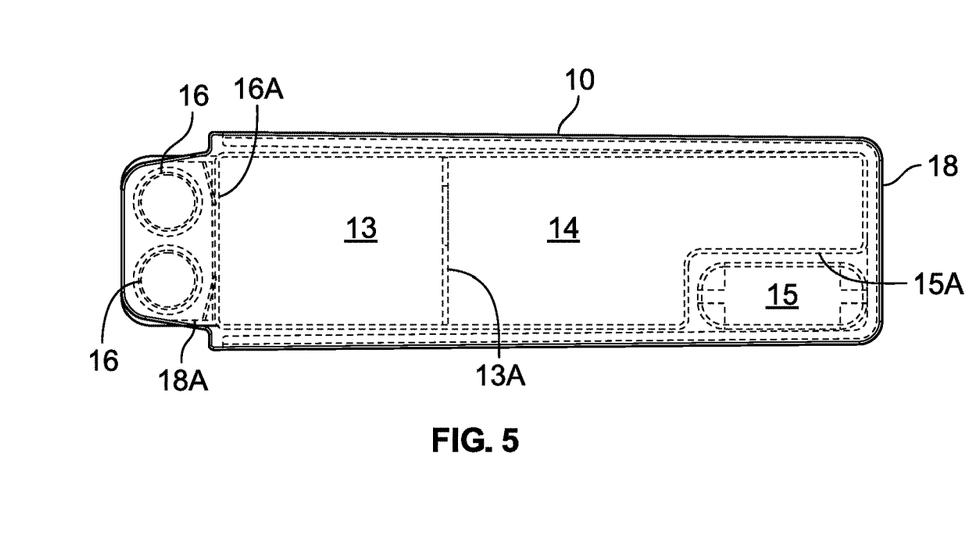
FIG. 5 is a top section view of the therapeutic procedural pack of FIGS. 1 to 3.
Figure 6:
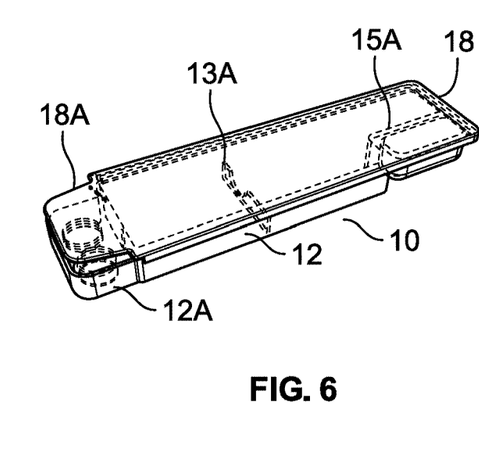
FIG. 6 is an isometric view of the therapeutic procedural pack of FIGS. 1 to 3 and FIG. 5.
Figure 7:
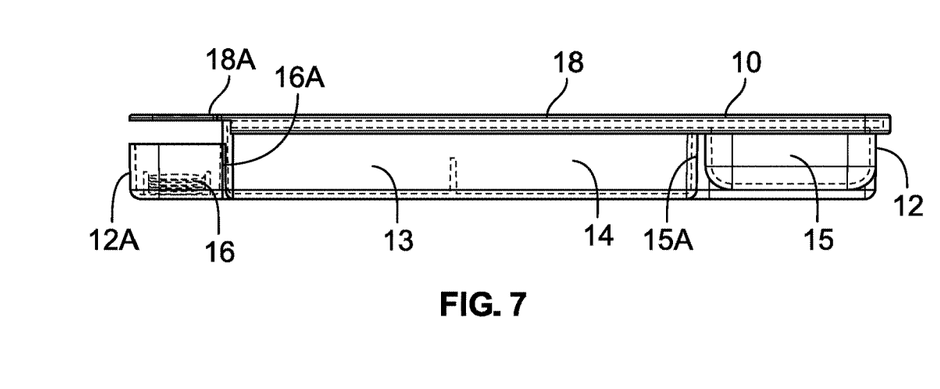
FIG. 7 is a side section view of the therapeutic procedural pack of FIGS. 1 to 3, 5 and 6.
Figure 8:
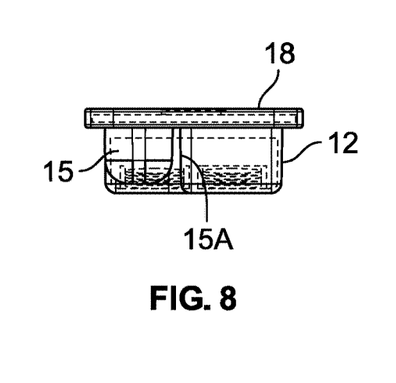
FIG. 8 is an end section view of the therapeutic procedural pack of FIGS. 1 to 3 and FIGS. 5 to 7.

Compartment 14 also accommodates two cartridges 40, 42 which respectively hold ampoules 140 and 142 with their sealing lids 140A and 142A between the disposal device 30 and a wall of the container 12. Ampoules 140 and 142 are filled to controlled volumes to prevent overdose or excessive dilution. Cartridges 40 and 42 comprise cylindrical non-return sleeves engaged with the ampoules 140, 142 by bayonet fit with the diameters of the ampoules 140 and 142 and cartridges 40 and 42 being selected accordingly. Three slots 40A are included in cartridges 40, 42 to embody the non-return feature and to enable a visual check of the ampoules 140, 142. FIG. 4 shows this feature for cartridge 40. Because of the non-return configuration of cartridges 40 and 42, tampering and damage to cartridges 40, 42 will be evident if replacement is attempted. Ampoules 140, 142 are preferably plastic though may be of glass in some cases. The contents of ampoules 140, 142 are packed under sterile conditions and remain sterile until sealing lids 140A and 142A are opened. Cartridges 40 and 42 respectively have threaded portions 41 and 43.

Referring also to FIG. 4, each cartridge 40, 42 also includes a RFID chip 47 which uniquely identifies the cartridge and its contents by a unique identification code or tag as known in the RFID communications art and antenna 47A which is included, in a location between the bottom of the ampoule 140, 142 and the base of the cartridge threaded portion, during the moulding step in a secure manner that minimizes risk of tampering. FIG. 4 shows location of RFID chip 47 and antenna 47A between the base 140B of ampoule 140 and the base of threaded portion 41. The RFID chip and tagging arrangement would be the same for ampoule 142 and cartridge 42. Procedural pack 10 includes a power source such as an electric battery to provide the necessary power for RFID and other communications (where provided).

RFID chip and transmitters 17, 47, 47A enables tracking of the container 12 and its ampoules 140 and 142 even if tampering does occur. Tampering behaviour has a pattern that is abnormal and can be detected through RFID tracking through the RFID system 47, 47A. Tracking provides data about use and transport which aids medical compliance and inventory management. As described above, correct matching of items for conducting the therapeutic procedure and containers is critical. RFID tagging also allows for the medicament stored in the ampoules 140, 142 to be authenticated prior to inclusion within the procedural pack 10 during manufacture enhancing medical safety.

RFID signal processing may also be used for control of the manufacturing process. For example, the manufacturing process could include a computer control system which match RFID signals from the RFID chip/transmitter 17 for container 12 and ampoules 140 and 142 and flag a fault if the signals do not correctly match, for example with signals stored in a pharmaceutical or vaccine supplier, regulatory or insurance database, with those required for the particular purpose of the procedural pack 10, for example including insulin when the required procedure is a vaccination. Erroneous packaging of a medicament or vaccine can thus be prevented.

Figure 3:
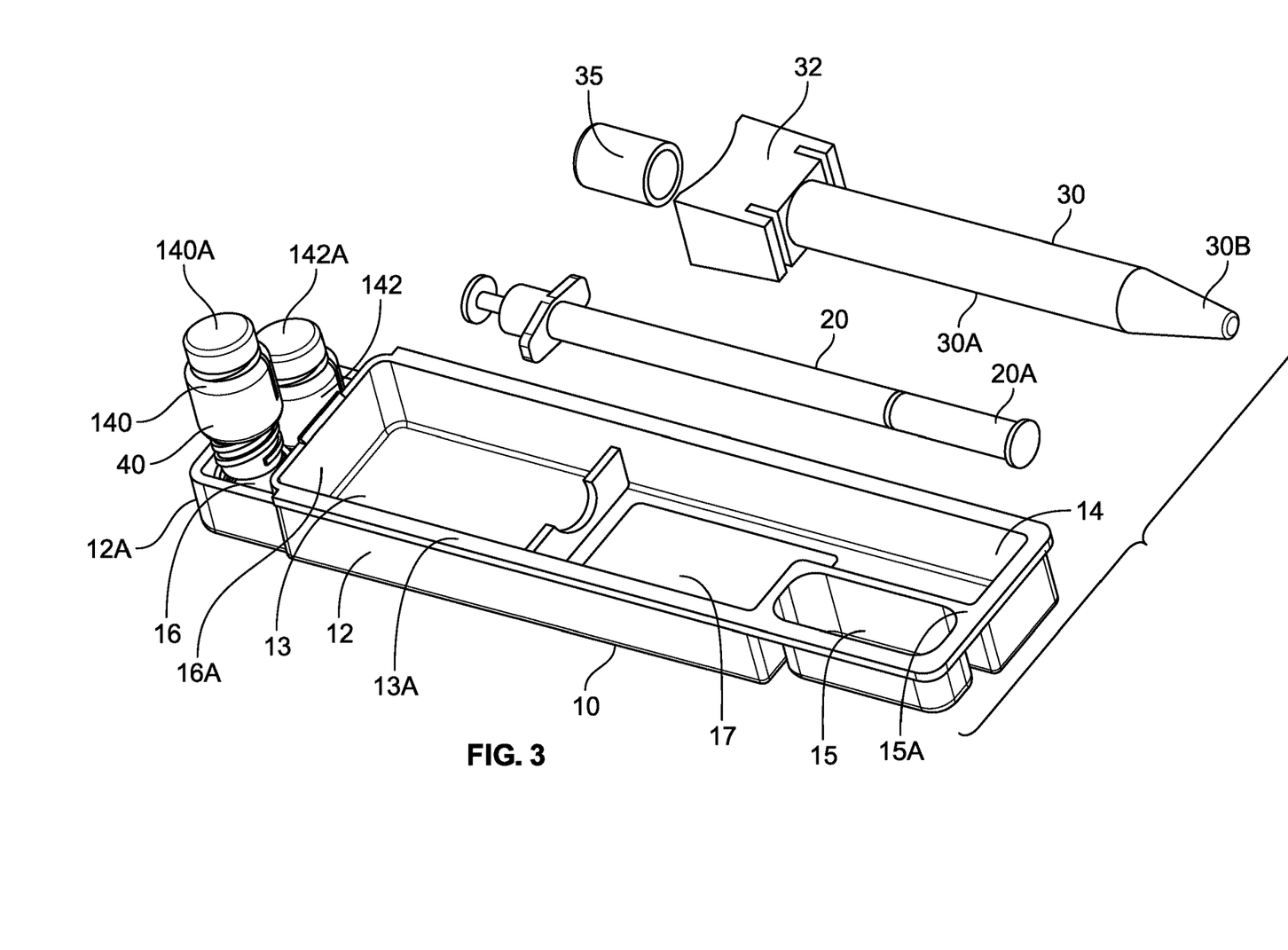
FIG. 3 shows an exploded isometric view of the therapeutic procedural pack of FIGS. 1 and 2.

Compartment 15 is a receptacle to allow preparation or rehydration of a medicament or vaccine with a diluent and it may be omitted if not required by the therapeutic procedure. As compartment 15 should be sterile, a purpose made insert or cover may be provided to achieve sterility. Compartment 15 is sized not to enable excessive dilution of medicament with diluent. Compartment 15 can also be used for storing other items, such as swabs, diluents or other items needed in a therapeutic procedure.

Compartments 16 are located in a portion 12A of the container, each compartment being threaded with matching thread to threaded portions 41 and 43 of cartridges 40 and 42. This allows fixing of cartridges 40 and 42 into position in threaded compartments 16 for preparation of the medicament or vaccine solution. Such fixing could, in some applications, occur after manufacture of therapeutic procedure pack 10 and at a convenient point in the distribution chain. For example, in some applications, the ampoules/cartridges may be supplied to a patient at a pharmacy or other collection centre. A quick check of whether the correct ampoules/cartridges have been supplied can be done by checking whether the threaded portions of ampoules/cartridges and compartments 16 engage. A 'no fit' indicates that the wrong ampoules or possibly the wrong procedural pack 10 have been provided.

All the above described items are packaged into container 12 under aseptic conditions. Container 12 is made of a suitable polymer or combination of polymers (though other materials such as metals or alloys could be used) and is fabricated by injection moulding. Ampoules 140 and 142 and cartridges 40 and 42 are formed in separate injection moulding steps to the moulding of container 20. Ampoules 140 and 142 may be filled by a high volume sterile packaging machine such as those available from Rommelag, Germany. Container 12 could have portions commonised for various applications, a helpful feature for optimising manufacturing costs and inventory management.

Figure 1:
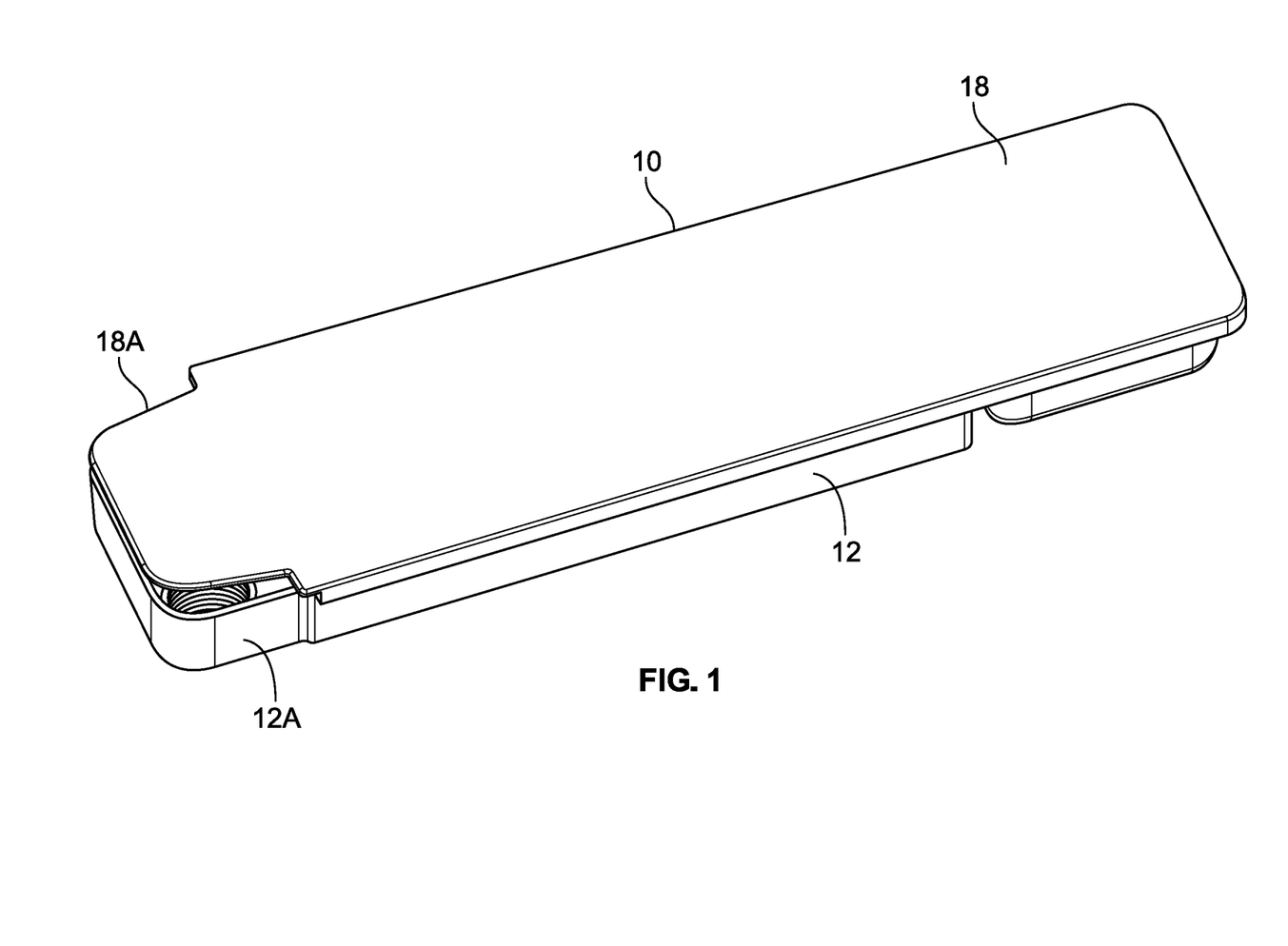
FIG. 1 shows an isometric view of the platform in the form of a therapeutic procedural pack according to one embodiment of the present invention and being in closed position.
Figure 2:
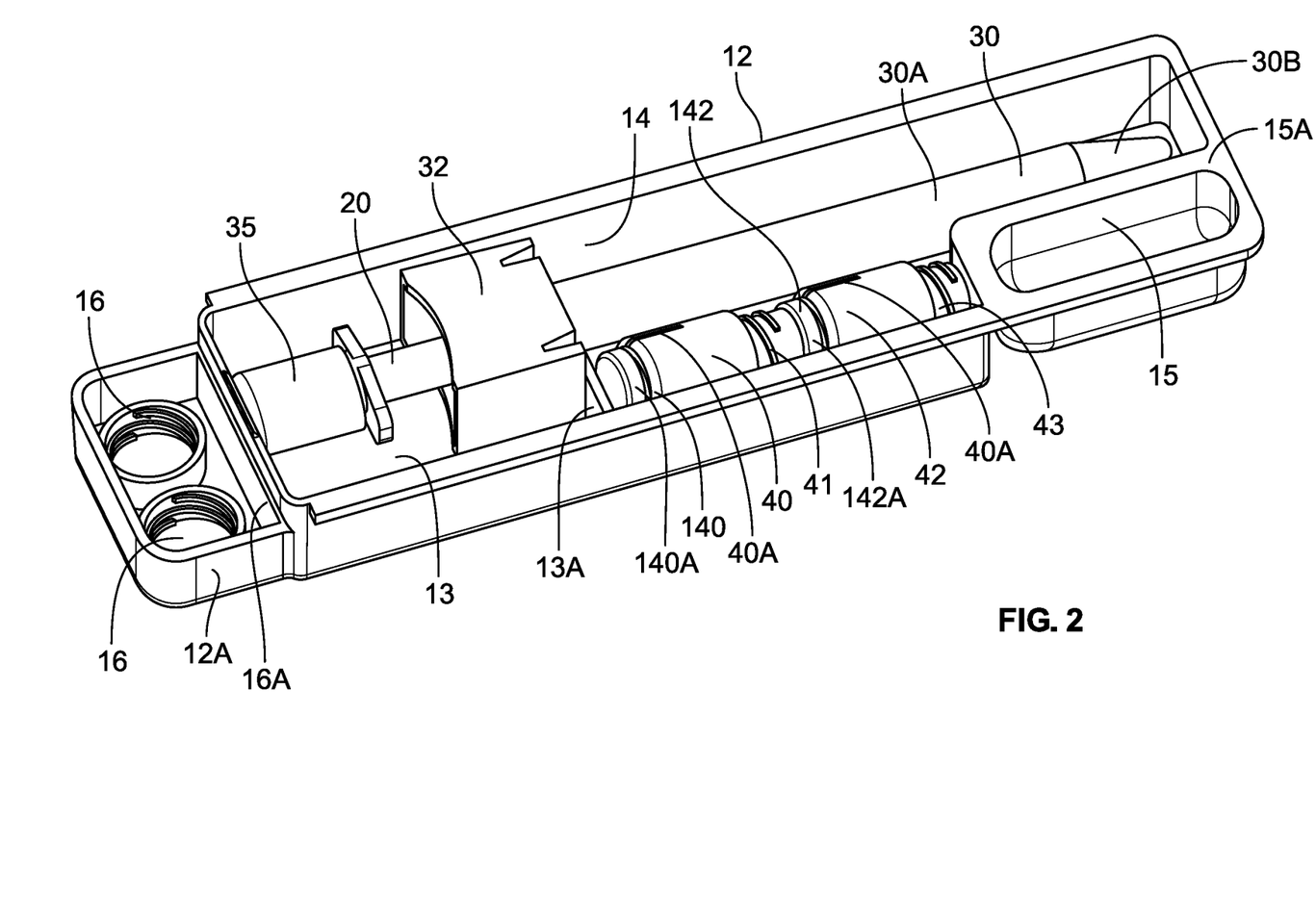
FIG. 2 shows the isometric view of the therapeutic procedural pack of FIG. 1 being in closed position.

Therapeutic procedural pack 10 is also provided with a lid 18 for container 12 though this could be replaced with a polymer or metal foil cover. Lid 18 has a portion 18A which can be snapped off or torn away to open lid 18 and access the contents of therapeutic procedural pack 10. However, lid 18 can be configured in a number of ways, including as a sliding lid. Lid 18 is reclosable at least for the disposal process. Container 12 could be further wrapped if required. Containers 12 are conveniently fabricated in bulk and, once filled with items, for example as described above are of convenient shape for packaging in standard box or carton containers.

A patient can obtain a therapeutic procedural pack 10 and perform the procedure of insulin administration in the usual way or another therapeutic procedure as instructed, for example as described with reference to FIG. 9 below. As the procedural pack 10 is carried home, the container 12 allows efficient and aseptic transport for the items required in the therapeutic procedure.

When a therapeutic procedure is to be performed, the patient snaps off portion 18A of the lid 18, removes the lid and gains access to the contents of the container 10. The procedure is performed following instructions included with the procedural pack 10. Syringe 20 is removed and the needle cover 20A removed. Cartridges 40 and 42 are removed and threaded into compartments 16. Lids 140A and 142A are removed, and the contents of medicament ampoule 140 drawn into the syringe 20. Then the contents of diluent ampoule 142 are drawn into syringe 20 to form the injectable. The patient or patient assistant injects the injectable.

Diluent/disinfecting solution may be provided in compartment 15 for swabbing. The use of a syringe 20 is described for purposes of illustration. Any injection device and mode of injection, for example by intravenous injection, intramuscular injection or injection by bifurcated needle is intended to be within the scope of the present disclosure.

Following the procedure, the syringe 20 should be fitted into the disposal device 30 and instruction may be provided to this effect. Ampoules 140 and 142 can also be re-stored in the container 12 which is then re-closed with lid 18 and disposed of in a safe manner.

The therapeutic procedural pack 10 may also be applied to other therapeutic procedures. Some procedures involve dilution of the medicament with a diluent. The therapeutic procedural pack 10 is designed to ensure that the correct dosage of medicament and correct quantity of diluent are provided, through sizing of the container 20, volume control over ampoules 140 and 142; and compartments for medicament and diluent ampoule and the RFID tagging and management system as described herein provides additional assurance. This avoids dosage and diluent errors. For example, the correct quantity of diluent may be 2 mL. The container 20 is then designed only to accommodate an ampoule of 2 mL capacity within one of its compartments, for example one or both of compartments 16.

The therapeutic procedural pack 10 has been designed through a holistic process with vials, ampoules and cartridges that are suitable for the therapeutic procedure being included in container 12 in a manner ensuring only the correct dosage of injectables and/or diluents and corresponding items to perform the procedure are supplied for each procedure. An additional advantage is the provision of a disposal device 50 allowing the safe disposal of the sharps in a technically proven manner. The therapeutic procedural pack 10 also acts to enhance the efficiency and methodology of injectable life cycle management and safe dispensing. The therapeutic procedural pack 10 also readily allows the safe transport and storage of injectables and sharps once dispensed.

Referring to FIG. 9, there is shown a system 100 for managing the manufacture, deployment and use of a number of therapeutic procedural packs 10 each of which may be as above described. Each procedural pack 10 has three RFID chips 17, 47 and 47A. RFID chips 47 and 47A had an important role during manufacture as described above. However, each chip 17, 47, 47A have a continuing use for tracking the locations of therapeutic packs 10, each being assigned a unique identification code. In one option, RFID tracking information providing locations of the therapeutic packs 10 may be communicated, in a manner known in the art of RFID systems, to a computer system 200 which controls the operation of system 100 through wireless communication channels 104. Computer system 200 may include a mainframe computer or system of mainframe computers as well as personal computing devices where needed. Other forms of computer may also be used, with parallel processing being adopted where required by the amount of data and processing required by the application for therapeutic packs 10. Multiple applications may be controlled by computer system 200.

The tracking information showing at least the location of the procedural packs 100 may be processed by processor 210 in a number of ways and the information is also stored in database 220 also forming part of the computer system 200. As to processing of the information from procedural packs 10, this may involve identification of trends in the movement of therapeutic procedural packs 10. Probability of location of procedural packs 10, and probable use, in a specific area may be mapped and correlated with health data for that area by processor 210 with deployment of procedural packs 10 focused on areas where there is most need for a therapeutic procedure. Where the therapeutic procedure involves a biosecurity threat countermeasure, areas of greatest threat may be identified and resources focused on management of the biosecurity threat in those areas. This may, in the case of an uncertain nature of a biosecurity threat, for example bacterial, viral or toxin derived from either, include assigning biological research personnel to those areas. Where the procedural packs 10 include sensors, of the "lab on a chip" nature or microfluidic sensors, such sensors may identify possible threats and such information may also be conveyed through communication channels 104 to the computer system 200 and processed by processor 210 to develop a control response. One control response may involve modifying the production rate (indicated by arrow 310) of procedural packs 10 by manufacturing plant 300 producing procedural packs 10 by an injection moulding process in response to processor 210 analysis of the received sensor signals. Alternatively, where there are a number of manufacturing plants 300 in different geographical locations, production rate may be modified according to demand assigned to each of the manufacturing plants 300. Such control may be completely automated. Such statistical process control may be supplemented by use of machine learning techniques by processing of information by the processor to improve the manufacture and/or efficacy of deployment of therapeutic packs as described herein while minimising costs, however measured, of such deployment or, indeed, non-deployment.

Computer system 200 may also initiate control responses in the form of requests to a medicament or vaccine manufacturing plant 400 for differing volumes of medicaments or vaccines to be provided to the manufacturing plant(s) 300 according to demand. These manufacturing plants may utilize RFID comparison between RFID chips 17, 47, 47A for each pack to ensure authentication and correct assignment to procedural packs Again, a number of manufacturing plants 400 may be involved in production of components such as vials, ampoules and other items to be contained within procedural packs 10. Production rate for such manufacturing plants 400 may also be controlled in response to demand signals from the computer system 200, such demand potentially being forecast by processor 210 following a model developed in real time or on the basis of previous analogous epidemics or health crises. The potential range of such health events is broad but such careful co-ordination—most likely by a multi-agency government response—is essential. To that end of careful information collection, processing and response co-ordination, where RFID tracking is used, the need to process data from multiple RFID chips or tags (17,47,47A, some potentially separating), potentially presents an identification and processing problem. An anti-collision algorithm, such as binary encoding, or other algorithm, for example as described in Liu and Su, "An Anti-Collision Algorithm for RFID based on An Array and Encoding Scheme", (2018), the contents of which are hereby incorporated herein by reference may therefore be implemented by computer system 200.

System 100 also allows for the involvement of a biological research centre 500 which may analyse sensor signals from computer system 200 as described above. Such input may be important where a biological or other agent has not yet been identified and an antidote may require development. Such input may also be important in the case where the agent is, for example a mutating virus. Processor 200 may send data, including real time data, to the research centre 500 and this may be used in developing an antidote, in particular a vaccine for example developed by an accelerated technique such as described in WO 2018176103, the contents of which are incorporated herein by reference. Such information may also be important in designing and manufacturing appropriately configured procedural packs 10 and, in particular, the required therapeutically effective items for inclusion within the procedural packs 10 and the configuration of compartments within the containers 12 to accommodate the items within the procedural packs 10. Thus, research centre 500 also sends data and even control signals to pack manufacturing plants 300 and therapeutically effective item manufacturing plants 400 to optimise production and minimise costs and wastage. This system allows a real time response to manufacturing capability and reduction in the lag to an efficacious response identified in the background discussion.

System 200 may involve use of a wireless communications network where the therapeutic procedural packs 10 include suitable electronic communications devices, such as included, for example, in laptops, smart devices or cell phones. Provision for USB or like download from therapeutic packs 10 could also be made. Computer system 200 is likely to be connected to manufacturing plants 300, 400 and research centre 500 through such wireless communications network though a wired network may also be practicable for communications between manufacturing plants 300, 400 and research centre 500. A secure wireless (or wired) communications network may be required due to the sensitivity of the data, especially where this cannot be anonymised, and because of the potential national security implications where the system 200 is used in response to a public health emergency or as a biosecurity threat countermeasure.

For ease of illustration, the wireless communication network channels are shown as channels 104 in FIG. 9. Where the procedural packs 10 allow messaging, the computer system 200 may send instructions to procedural packs 10 (or mobile phones or other communications devices correlated with them) including, without limitation, instructions for opening a procedural pack 10 or indicating when pack use is required. For example, and as described above, the procedural packs 10 could be issued to protect a population against a possible biosecurity threat. However, the relevant authority may not yet have evidence that the population must use procedural packs 10 for protection. When such evidence is received, instructions may be issued for the population or segment(s) of that population, segments being determined by geographical location or processing of usage data by processor 210 of computer system 200 as described above. Such instructions are most conveniently sent through a wireless communications network from the computer system 200 to individual procedural packs 10 particularly where a mobile phone cannot be correlated with a procedural pack 10, could include activation of the therapeutic pack 10, for example by providing access to the pack 10. This allows greater precision over the therapeutic response to the threat and avoids costly and potentially risky use of procedural packs 10, such costs highly desirably being minimised.

In a further embodiment, the computer system 100 may also initiate a control response in terms of modifying a step in a pack manufacturing process in a manufacturing plant 300 so that packs include the necessary therapeutically effective item(s) to counter the threat. For example, the computer system 100 may control a 3D printing facility or injection moulding plant to produce procedural packs 10 with the required compartments and items corresponding to a therapeutic procedure to be conducted. Such items may include an antidote to a biosecurity threat.

The computer system 200 may also control the logistical mode of deployment of packs 10 to a target population, for example by controlling operation of autonomous vehicle, robot, drone or like computer controllable transport means which is particularly advantageous where the threat is highly contagious, for example in the case of a viral infection.

Modifications and variations to the platform and system described here will be understood to skilled readers of this disclosure. Such modifications and variations are deemed within the scope of the present invention.

What is claimed:

1. A method for managing the use of portable therapeutic platforms for a therapeutic procedure comprising the steps of:
    (a) providing a plurality of therapeutic procedural packs, each therapeutic procedural pack comprising at least one vaccine or medicament and at least one further therapeutically effective item required to conduct the therapeutic procedure including the administration of the vaccine or medicament to a patient and an electronic communications device having a unique identification code for receiving and transmitting information about an environment surrounding and including each platform;
    (b) transferring information about the environment surrounding and including each therapeutic procedural pack between the electronic communications device of each therapeutic procedural pack and a computer system including a processor which processes said information in real time; and
    (c) initiating an automated control response to, when processed, said information transferred from said plurality of therapeutic procedural packs, wherein said electronic communications device of each therapeutic procedural pack communicates with the computer system so that information is communicated between each therapeutic procedural pack and the processor of the computer system; and
wherein said processed information enables control over manufacture of therapeutic procedural packs and deployment of therapeutic procedural packs to different geographic segments; and
wherein said computer system is configured to initiate said automated control response by modifying a step in a therapeutic procedural pack manufacturing process so that said therapeutic procedural packs include determined therapeutically effective items.

2. The method of claim 1, wherein each said therapeutic procedural pack allows administration of a medicament or vaccine to a patient by injection in single or multiple episodes, and comprises a plurality of compartments for holding a group of therapeutically effective items consisting of a vial of a vaccine and an injector, comprising, from manufacture through to administration of the medicament or vaccine to a patient:
    tracking information from an electronic communications device for each said therapeutic procedural pack; and
    tracking information from a further at least one electronic communications device for the group of therapeutically effective items.

3. The method of claim 1, wherein said information includes information about the use of the pack including information from sensors detecting when, how and where the items contained within the pack are used.

4. The method of claim 1, wherein the computer system receives informational inputs from each of said plurality of therapeutic procedural packs showing how, when and where the packs are used.

5. The method of claim 1, wherein said electronic communications device includes a device forming part of a passive or active RFID system, at least one RFID chip and antenna being included within a therapeutic procedural pack.

6. The method of claim 5, wherein tampering with a therapeutic procedural pack is detected by said RFID system.

7. The method of claim 1, wherein the platform includes at least one analytic device which allows analysis of items included within the pack or analysis of the environment surrounding and including the pack.

8. The method of claim 7, wherein the analytic device tests diluents, injectables or pharmaceutical compositions to check that such are safe for administration in terms of chemical composition and dosage.

9. A method for managing the use of portable therapeutic platforms for a therapeutic procedure comprising the steps of:
   (a) providing a plurality of therapeutic procedural packs, each therapeutic procedural pack comprising a therapeutically effective item required to conduct the therapeutic procedure and an electronic communications device having a unique identification code for receiving and transmitting information about an environment surrounding and including each platform;
   (b) transferring information about the environment surrounding and including each therapeutic procedural pack between the electronic communications device of each therapeutic procedural pack and a computer system including a processor which processes said information in real time; and
   (c) initiating an automated control response to, when processed, said information transferred from said plurality of therapeutic procedural packs wherein said electronic communications device of each therapeutic procedural pack communicates with the computer system so that information is communicated between each therapeutic procedural pack and the processor of the computer system; and
   wherein said processed information enables control over manufacture of therapeutic procedural packs and deployment of therapeutic procedural packs to different geographic segments; and
   wherein said computer system is configured to initiate said automated control response by modifying a step in a therapeutic procedural pack manufacturing process so that said therapeutic procedural packs include determined therapeutically effective items.

10. The method of claim 9, wherein said therapeutically effective item includes a medicament for treatment of diabetes.

11. The method of claim 10, wherein said medicament is insulin.

* * * * *